United States Patent
Volgas et al.

(10) Patent No.: US 6,939,555 B2
(45) Date of Patent: Sep. 6, 2005

(54) MANUFACTURE AND USE OF AN DEPOSITION AID

(75) Inventors: Greg Volgas, Bartlett, TN (US); Johnnie R. Roberts, Memphis, TN (US)

(73) Assignee: Helena Holding Company, Wilmington, DE (US)

( * ) Notice: Subject to any disclaimer, the term of this patent is extended or adjusted under 35 U.S.C. 154(b) by 437 days.

(21) Appl. No.: 09/734,637

(22) Filed: Dec. 12, 2000

(65) Prior Publication Data

US 2002/0108415 A1 Aug. 15, 2002

Related U.S. Application Data

(60) Provisional application No. 60/177,420, filed on Jan. 21, 2000.

(51) Int. Cl.$^7$ .................. A01N 25/04; A01N 25/24; A61K 47/36; B01F 3/12
(52) U.S. Cl. .................. 424/407; 514/782; 504/363; 504/366; 516/31; 516/53; 516/105
(58) Field of Search ................. 504/363, 366; 516/105, 31, 53, 103; 137/13; 508/471; 424/DIG. 8, 407; 514/782; 106/205.5; 536/114

(56) References Cited

U.S. PATENT DOCUMENTS

| | | | |
|---|---|---|---|
| 2,828,261 A | * 3/1958 | Milberger et al. | |
| 3,287,189 A | * 11/1966 | Wilson et al. | 149/8 |
| 3,360,356 A | * 12/1967 | Vartiak | 504/361 |
| 3,776,248 A | * 12/1973 | Titus | 137/13 |
| 3,911,122 A | * 10/1975 | Drabek et al. | 424/DIG. 8 |
| 4,227,911 A | 10/1980 | Leonard et al. | 71/77 |
| 4,571,422 A | * 2/1986 | Symes et al. | 536/114 |
| 4,717,488 A | * 1/1988 | Seheult et al. | 536/114 X |
| 4,803,264 A | * 2/1989 | Krijnen et al. | 536/114 |
| 4,828,034 A | * 5/1989 | Constien et al. | 166/308.4 |
| 5,045,588 A | * 9/1991 | Arranaga | 524/445 |
| 5,178,795 A | 1/1993 | Roberts | |
| 5,234,919 A | 8/1993 | Roberts | 514/119 |
| 5,393,791 A | 2/1995 | Roberts | 514/762 |
| 5,466,458 A | * 11/1995 | Martin et al. | 424/DIG. 8 |
| 5,508,249 A | 4/1996 | Narayanan et al. | 504/116 |
| 5,523,014 A | * 6/1996 | Dolan et al. | 516/103 X |
| 5,525,575 A | 6/1996 | Chamberlain | 504/116 |
| 5,529,975 A | 6/1996 | Chamberlain | 504/116 |
| 5,580,567 A | 12/1996 | Roberts | 424/405 |
| 5,725,630 A | 3/1998 | Roberts et al. | 71/11 |
| 5,741,502 A | 4/1998 | Roberts | 424/405 |
| 5,798,112 A | * 8/1998 | Heitz et al. | 424/407 X |
| 5,863,861 A | 1/1999 | Einziger | 504/116 |
| 5,877,112 A | 3/1999 | Roberts et al. | 504/116 |
| 5,906,961 A | 5/1999 | Roberts et al. | 504/116 |
| 5,964,917 A | 10/1999 | Latting | 71/49 |
| 5,977,030 A | * 11/1999 | House | 516/53 X |
| 6,100,225 A | * 8/2000 | Kalhan et al. | 508/471 X |
| 6,241,795 B1 | 6/2001 | Svec et al. | 71/11 |
| 6,277,893 B1 | * 8/2001 | Babenko | 516/53 X |
| 6,432,155 B1 | 8/2002 | Swazey et al. | 71/27 |

* cited by examiner

*Primary Examiner*—Daniel S. Metzmaier
(74) *Attorney, Agent, or Firm*—Connolly Bove Lodge & Hutz, LLP

(57) ABSTRACT

The invention pertains to a method for increasing the activity of agrichemicals and controlling their drift by specially formulating an deposition agent with fertilizer. This unique combination has been seen to allow lower use rates of fertilizers as pesticide efficacy enhancers and improved deposition of sprays.

16 Claims, No Drawings

MANUFACTURE AND USE OF AN DEPOSITION AID

This application claims benefit to provisional Ser. No. 60/177,420 Filed Jan. 21, 2000, which is incorporated by reference in its entirety for all useful purposes.

BACKGROUND OF THE INVENTION

Polyacrylamide or polyvinyl polymers and natural gums, like guar gum, have been used for several years as deposition or drift reducing agents. U.S. Pat. No. 5,964,917 has shown the benefits of nitrogenous fertilizers, non-derivatized guar gum, cationic guar gum, and non-cationic guar gum, and mixtures, thereof and a silicone defoamer. One problem of this patented formulation is that it must include a silicone defoamer. Another problem with this formulation is the reliance on nitrogenous fertilizers. This formulation is also restricted unnecessarily to a dry form. The amount of nitrogenous fertilizer required is unnecessarily high with relation to the amount of guar. Finally, this prior art is restricted to using non-derivatized guar gum, cationic guar gum, and non-cationic guar gum, and mixtures, thereof. It would be beneficial to use other less expensive drift control agents or deposition agents.

A product currently on the market contains 1% of a polyacrylamide polymer and roughly 10–20% of ammonia salts (sulfate or carboxylic acid) and 1–2% a silicone defoamer. This product is a liquid and does not perform adequately in some instances due to the low level of polyacrylamide polymer used.

Other liquid products currently available contain 30–35% ammonia sulfate, 1–2% polyacrylamide and a silicone defoamer at 1–3%.

Other dry products currently being marketed have some of the same limitations of the patented product described above. Specifically, these products contain about 1–5% of polyacrylamide or polyvinyl polymers, 90–96% of ammonia salts (Ammonia carboxylate, sulfate and polyacrylate) and 1–2% of a silicone defoamer.

Another liquid product contains 1–2% modified guar gum, 30–35% ammonia sulfate, and no defoamer. A similar product contained the same amounts as this one, but also included 5–10% of diethylene glycol as an anti-freeze.

Another liquid product contains 20–30% ammonia sulfate and water, and in another layer of the liquid, contains aromatic acids and aliphatic petroleum distillates.

Another dry product on the market contains 5–10% of a blend of polyacrylamide polymers and xantham gum, and 90–95% ammonia sulfate and 1–5% silicone defoamer.

In U.S. Pat. Nos. 5,529,975 and 5,525,575, Chamberlain describes the use of oils and water to produce stable dispersions of acrylamide polymers for deposition and drift control.

SUMMARY OF THE INVENTION

The present invention is a homogenous agricultural composition containing at least one fertilizer or oil and at least one deposition agent. Our new discovery is that lower rates of nitrogenous fertilizers and correspondingly higher rates of non-derivatized guar gum, cationic guar gum, and non-cationic guar gum, and mixtures, thereof can also provide benefits to agricultural applicators. Furthermore, we have discovered alternatives to nitrogenous fertilizers that when combined with non-derivatized guar gum, cationic guar gum, and non-cationic guar gum, and mixtures, thereof, provide beneficial spray characteristics. Also, we have discovered that other deposition agents can be added to fertilizers to enhance their efficiency. The use of defoamers is helpful, but not required. We have also discovered a way to deliver the benefits of natural gums in liquid oil-based compositions. In many cases, the oil provides the same benefits as the fertilizer; i.e. increased pesticide efficacy and easier use of the deposition and drift control agent.

The nitrogenous fertilizers of the present invention include, but are not limited to:

Ammonia salts; including but not limited to:

Ammonium sulfate,

Ammonium bisulfate,

Ammonium salts of carboxylic acids,

Ammonium chloride,

Ammonium carbonate,

Ammonium phosphate,

Ammonium nitrate,

Ammonium thiosulfate and

Ammonium hydroxide,

Urea-Ammonia nitrate solutions,

Urea;

Urea phosphate;

Potassium nitrate and

Urea-formaldehyde polymers.

Others included are described from the AAPFCO guide, 1998, (Association of American Plant Food Control Officials, Official Publication Number 51) which is incorporated by reference in it's entirety for all useful purposes.

N-1. Ammortiated Superphosphate is a product obtained when superphosphate is treated with ammonia or with solutions which contain ammonia and other compounds of nitrogen. The guaranteed percentages of nitrogen and of Available Phosphate shall be stated as part of the name. (Official 1993)

N-2. Ammonium Nitrate is chiefly the ammonium salt of nitric acid. It shall contain not less than thirty-three percent (33%) nitrogen, one-half of which is in the ammonium form and one-half in the nitrate form. (Official 1951)

N-3. Calcium Nitrate is chiefly the calcium salt of nitric acid. It shall contain not less than fifteen percent (15%) nitrate nitrogen. (Official 1951)

N-4. Nitrate of Potash (potassium nitrate) is chiefly the potassium salt of nitric acid. It shall contain not less than twelve percent (12%) nitrogen and forty-four percent (44%) Soluble Potash. (Official 1951)

N-5. Nitrate of Soda (sodium nitrate) is chiefly the sodium salt of nitric acid. It shall contain not less than sixteen percent (16%) nitrate nitrogen and twenty-six percent (26%) sodium. (Official 1952)

N-6. Nitrate of Soda and Potash (sodium and potassium nitrate) is chiefly the sodium and potassium salts of nitric acid. It shall contain not less than fifteen percent (15%) nitrate nitrogen, ten percent (10%) soluble potash and eighteen percent (18%) sodium. (Official 1952)

N-7. Sulfate of Ammonia (ammonium sulfate) is chiefly the ammonium salt of sulfuric acid. It shall contain not less that, twenty and five-tenths percent (20.5%) nitrogen. (Official 1951)

N-8. Ammonium Sulfate Nitrate is a double salt of ammonium sulfate and a ammonium nitrate which are present in equal molecular proportions. It shall contain not less than twenty-six percent (26%) nitrogen, one-fourth of which is in nitrate form and three fourths in the ammonium form. (Official 1954)

N-9. Acidulated Fish Tankage (acidulated fish scrap) is the rendered product derived from fish and treated with sulfuric acid. (Official 1950)

N-10. Activated Sewage Products are those made from sewage freed from grit and coarse solids and aerated after being inoculated with micro organisms. The resulting flocculated organic matter is withdrawn from the tanks, filtered with or without the aid of coagulants, dried, ground and screened. (Official 1950)

N-11. Bat Guano is partially decomposed bat manure. (Official 1951)

N-12. Cyanamide is a commercial product consisting principally of calcium cyanamide (CaNCN) and carbon and it shall contain not less than nineteen and five tenths percent 19.5%) nitrogen.

N-13. Dried Blood is the collected blood of slaughtered animals, dried and ground and containing not less than twelve percent (12%) nitrogen. (Official 1950)

N-14. Animal Manures are the excreta of animals together with whatever bedding materials are needed to follow good dairy barn, feedlot, poultry house, etc., practice in order to maintain proper sanitary conditions. (Official 1991)

N-15. Garbage Tankage is the rendered, dried and ground product derived from waste household food materials. (Official 1951)

N-16. Hoof and Horn Meal is processed dried, ground hoofs and horns. (Official 11951)

N-17. Peat is partly decayed vegetable matter of natural occurrence. It is composed chiefly of organic matter that contains some nitrogen of low activity. (Official 1951)

N-18. Fish Tankage (fish scrap, dry ground fish, fish meal fertilizer grade) is the dried ground product derived from rendered or unrendered fish. (Official 1950)

N-19. Process Tankage is a product made under steam pressure from crude inert nitrogenous materials, with or without the use of acids or bases, for the purpose of increasing the activity of nitrogen. These products shall be called "Process Tankage" with or without further qualification. The water insoluble nitrogen in these products shall test at least fifty percent (50%) active by the alkaline, or eighty percent (80%) by the neutral permanganate method. (Official 1994)

N-20. Tankage (without qualification) is the rendered, dried, and ground by-product, largely meal and bone from animals (slaughtered or that have died otherwise). (Official 1950)

N-21. Sheep Manure Wool Waste is the by-product from wool-carding establishments consisting chiefly of sheep manure, seeds, and wool fiber. (Official 1961)

N-22. Crude, Inert, or Slow-Acting Nitrogenous Materials are unprocessed organic substances relatively high in nitrogen but having a very low value as plant food and showing a low activity by both the alkaline and neutral permanganate methods, (below 50% and 80% respectively). (Official 1964)

N-23. Urea is the commercial synthetic acid amide of carbonic acid and it shall contain not less than forty-five percent (45%) nitrogen. (Official 1966)

N-24. Ureaform Fertilizer Materials (sparingly soluble) are reaction products of urea and formaldehyde which contain at least thirty-five percent (35%) nitrogen, largely in insoluble but slowly available form. The water insoluble content shall be at least sixty percent (60%) of the total nitrogen. The water insoluble nitrogen in these products shall have an activity index of not less than forty percent (40%) when determined by the appropriate AOAC International method. (Official 1984)

N-25. Urea-Formaldehyde Products (sparingly soluble) are reaction products of urea and formaldehyde which contain less than thirty-five percent (35%) nitrogen, largely in insoluble but slowly available form. They shall have the percentage of total nitrogen as part of the product name; for example: 20% N Urea-Formaldehyde. The water insoluble Nitrogen shall be at least sixty percent (60%) of the total nitrogen. The activity index of the water insoluble nitrogen shall be either (1) not less than forty percent (40%) by the AOAC International method for Urea-formaldehyde Products or (2) not less than fifty percent (50%) by the AOAC International alkaline permanganate method or eighty percent (80%) by the neutral permanganate method. (Official 1984)

N-26. Isobutytlidiene Diurea—A condensation product of isobutyraldehyde and urea having a minimum total nitrogen content of thirty percent (30%). It is a source of slowly available nitrogen by virtue of particle size, solubility decreasing with increase in particle size. Material conforming to the description of a "granular fertilizer" will have ninety percent (90%) of its nitrogen content in the water-insoluble form prior to grinding as tested by AOAC International Method 945.01 (15th Edition). (Official 1986)

N-27. Sulfur Coated Urea (SCU)—A coated slow release fertilizer consisting of urea particles coated with sulfur. The product is usually further coated with a sealant 2% to 3% of total weight) and a conditioner (2% to 3% of total weight). It typically contains about thirty percent (30%) to forty percent (40%) nitrogen and about ten percent (10%) to thirty percent (30%) sulfur. (Official 1980)

N-28. Urea-Formaldehyde Products (water soluble) are reaction products of urea and formaldehyde which contain at least thirty percent (30%) nitrogen, largely in water soluble form. Some slowly available nitrogen products are present. Stable aqueous solutions may be prepared from these materials. The reaction products shall contain a maximum of fifty-five percent (55%) free urea, with the remainder of the urea being chemically combined as methylolureas, methylolurea ethers, and/or methylenediurea (MDU) and dimethylenetriurea (DMTU). (Official 1984)

N-29. Methylenediurea (MDU) is a water soluble condensation product resulting from the reaction of one molecule of formaldehyde with two molecules of urea, with the elimination of one molecule of water. It has a minimum total nitrogen content of forty-two percent (42%) and is a source of slowly available nitrogen. (Official 1984)

N-30. Dimethylenetriurea (DMTU) is a water soluble condensation product resulting from the reaction of two molecules of formaldehyde with three molecules of urea, with the elimination of two molecules of water, and having a minimum total nitrogen content of forty-one percent (41%). It is a source of slowly available nitrogen. (official 1984)

N-31. Dicyanodiamide (cyanoquanidine) is a water soluble organic compound of formula $C_2H_4N_4$ which contains at least sixty-five percent (65%) nitrogen. It s a source of slowly available nitrogen. (Official 1985)

N-32. Polymer Coated Urea (PCU) is a coated slow release fertilizer consisting of urea particles coated with a polymer (plastic) resin. It typically contains about forty percent (40%) nitrogen, it is a source of slowly available nitrogen. (Official 1990)

N-33. Triazone is a water soluble compound of formula $C_3H_7N_3O$ which contains at least forty-one percent (41%) total nitrogen. (CAS No. 7098-14-6, 1,3,5-triazin-2-one, tetrahydro-S-triazone.) (Official 1989)

N-34. Melamine is a sparingly soluble organic compound of formula $C_5H_6N_6$ which contains at feast sixty-six percent (66%) nitrogen. (GAS No. 108-78-1 2,4,6-triamino-1,3, 6-triazine,triamino-s-triazine) (Official 1989)

N-35. Urea-Triazone Solution—is a stable solution resulting from controlled reaction in aqueous medium of urea, formaldehyde, and ammonia which contains at least twenty-five percent (25%) total nitrogen. The solution shall contain no more than forty percent (40%) nor less than five percent (5%) of total nitrogen from unreacted urea and not less than forty percent (40%) from triazone, All other nitrogen shall be derived from water soluble, dissolved reaction products of the above reactants. It is a source of slowly available nitrogen. (Official 1990)

N-36. Oxamide (fertilizer grade) is the diamide of oxalic acid of the form $C_2H_4N_2O_2$ which contains twenty-eight to thirty-two percent nitrogen (28%–32%). It is a source of slowly available nitrogen. (Official 1990)

N-37. Ammonium Thiosuftale (fertilizer grade) is a commercial product composed principally of $(NH_4)S_2O_3$. The guaranteed percentages of nitrogen and sulfur shall be stated as part of the name. (Official 1990)

Phosphate Products ($P_2O_5$)

P-1. Phosphate is the amount of pentavalent phosphorus {P(V)} present in the material calculated as phosphorus pentoxide ($P_2O_5$). (Official 1997)

P-2. Available Phosphate is the sum of the water soluble and the citrate-soluble phosphate. (Official 1993)

P-3. Ammoniated Superphosohate is a product obtained when superphosphate is treated with ammonia or with solutions which contain ammonia and other compounds of nitrogen. The guaranteed percentages of nitrogen and of available phosphate shall be stated as part of the name. (Official 1993)

P-4. Ammonium Phosohate (fertilizer grade) is a product obtained when phosphoric acid is treated with, ammonia (anhydrous or aqueous), and consists principally of monoammonium phosphate and diammonium phosphate or a mixture of these two salts, The guaranteed percentage of nitrogen and of available phosphate shall be stated as part of the name. (Official 1993)

P-5. Ammonium Phosohate-Sulfate (fertilizer grade) is a product obtained when a mixture of phosphoric acid and sulfuric acid is treated with ammonia. It consists principally of a mixture of ammonium phosphate and ammonium sulfate. The guaranteed percentages of nitrogen and of Available Phosphate shall be stated as apart of the name (Official 1993)

P-6. Basic Lime Phosphate (lime-based superphosphate) is a superphosphate to which liming materials have been added in a quantify at least six percent (6% calcium carbonate equivalent in excess of the quantity required to convert all water soluble phosphate to the citrate-soluble form. (Official 1951)

P-7. Basic Phosphate Slag is a by-product obtained in the manufacture of steel from phosphatic iron ores. The product shall contain no admixture of materials other than those resulting from the original process of manufacture. It shall contain not less than twelve percent (12%) of total phosphate, of which at least eighty percent (80%) shall be available phosphate. It shall be ground so that not less than seventy percent (70%) of the material passes through a U.S. Standard No. 100 sieve (150 $\mu$m opening) and ninety percent (90%) passes through a U.S. Standard No. 50 sieve (300 $\mu$m opening). Any basic phosphate slag not conforming to this definition shall be designated low phosphate. (Official 1993)

P-8. Citrate-Soluble Phosohate is that part of the total phosphate in a fertilizer that is insoluble in water but soluble in a solution of citrate of ammonia according to the method adopted by the AOAC International. (Official 1993)

P-9. Dicalcium Phosphate is a manufactured product consisting chiefly of dicalcic salt of phosphoric acid, (Official 1951)

P-10. Acidulated Bone is ground bone or bone meal that has been treated with sulfuric acid. (Official 1951)

P-11. Ground Raw Bone is ground animal bones that have not been previously steamed under pressure, heated, or otherwise manipulated. (Official 1984)

P-12. Bone Meal is ground animal bones that have been previously steamed under pressure, heated, or rendered sterile in some other acceptable manner. (Official 1997)

P-13. Phosohate Rock is a natural rock containing one or more calcium phosphate minerals of sufficient purity and quantity to permit its use, either directly or after concentration, in the manufacture of commercial products. (Official 1952)

P-14. Precipitated Phosphate is a product consisting mainly of dicalcium, phosphate obtained by neutralizing with calcium hydroxide the acid solution of either phosphate rock or processed bone. (Official 1961)

P-15. Superphosphate a product obtained when rock phosphate is treated with either sulfuric acid, phosphoric acid, or a mixture of those acids. The guaranteed percentage of available phosphate shall be stated as a part of the name. (Official 1993)

P-16. Soft Phosohate with Colloidal Clay is a very finely divided low-analysis by-product from mining Florida rock phosphate by a hydraulic process in which the colloidal materials settle at points in artificial ponds and basins farthest from the washer, and are later removed after the natural evaporation of the water. (Official 1951)

P-17. Calcium Metaphosohate is a vitreous product substantially free from crystalline phosphates, resulting from the treatment of phosphate rock with gaseous phosphorus pentoxide at high temperatures. The guaranteed percentage of available phosphate shall be stated as part of the name. (Official 1993)

P-18. Polyphosphates is a general term pertaining to salts of any of a series of polyphosphoric acids, whose molecular structure contain two or more phosphorus atoms linked by oxygen. Solutions may contain several species such as orthophosphates, pyrophosphates, and polyphosphates containing three (3) or more phosphorus atoms, commonly known as tripolyphosphates or tetrapolyphosphates and water. (Official 1976)

P-19. Superphosphonic Acid is the acid form of polyphosphates, consisting of a mixture of orthophosphoric and polyphosphonic acids. Species distribution varies with concentration, typically sixty-eight to eighty-three percent (68 to 83%) $P_2O_5$. (Official 1976)

P-20. Calcined Phosohate is phosphate rock which has been heated, with or without one or more catalysts or reagents, sufficient to volatilize and remove most or all organic, carbonate, fluoride and other impurities, and/or thermally altered to more available calcium phosphate compounds, depending on the process. A significant portion of the phosphate is citrate soluble and such percentage shall be stated as part of the brand name. Included are products known as fused tricalcium phosphate, defluorinated phosphate, rhenania phosphate and various trade names. (Official 1994)

P-21. DAP (fertilizer grade) is a product composed of ammonium phosphates, principally diammonium phosphate, resulting from the ammoniation of phosphoric acid. It may contain up to 2% non-ammoniacal nitrogen. The guaranteed percentage of nitrogen and available phosphate shall be stated as part of the name. (Official 1993)

P-22. MAP (fertilizer grade) is a product composed of ammonium phosphates, principally monoammonium phosphate, resulting from the ammoniation of phosphoric acid. The guaranteed percentage of nitrogen and available phosphate shall be stated as part of the name. (Official 1991)

P-23. Magnesium Ammonium Phosphate is chiefly the ammonium and magnesium double salt of orthophosphonic acid and its condensates. It shall contain not less than seven percent (7%) nitrogen, thirteen percent (13%) magnesium and forty percent (40%) available phosphate. It is a source of slowly available nitrogen, magnesium, and available phosphate. (Official 1996)

P-24. Magnesium Potassium Phosphate is chiefly the magnesium and potassium double salt of orthophosphoric acid and its condensates. It shall contain not less than twenty one percent (21%) soluble potash, twelve percent (12%) magnesium and thirt six percent (36%) available phosphate. It is a source of slowly available potash, magnesium and available phosphate. (Official 1995)

The non-nitrogenous fertilizers of the present invention include, but are not limited to:

Potash sources, including but not limited to
Potassium phosphate (mono- or di-),
Potassium carbonate,
Potassium chloride,
Potassium sulfate,
Potassium salts of carboxylic acids,
Potassium phosphite, Others included are described AAPFCO guide, 1998 again, which is incorporated by reference in it's entirety for all useful purposes.

Phosphate sources, including but not limited to
Phosphoric acid,
Phosphorous acid, Others included which are incorporated by reference in its entirety from the AAPFCO guide, 1998.

AAPFCO discloses the following Potash sources which include

K-1. The term Potash designates potassium oxide ($K_2O$). (Official 1957)

K-2. Soluble Potash is that portion of the potash contained in fertilizer on fertilizer materials which is soluble in aqueous ammonium oxalate, aqueous ammonium citrate, or water, according to an applicable AOAC International method. (Official 1986)

K-3. Kainit is a potash salt containing potassium and sodium chlorides and sometimes sulfate of magnesia with not less than twelve percent (12%) soluble potash ($K_2O$). (Official 1975)

K-4. Mine Run Potash Salts are potash salts containing a high percentage of chloride and from twenty percent (20%) to thirty percent (30%) soluble potash ($K_2O$). (Official 1951)

K-5. Muriate of Potash (commercial potassium chloride) is a potash salt containing forty-eight percent (48%) to sixty-two percent (62%) soluble potash ($K_2O$) chiefly s chloride. (Official 1951)

K-6. Nitrate of Potash (potassium nitrate) is chiefly the potassium salt of nitric acid. It shall contain not less than twelve percent (12%) nitrogen and forty-four percent (44%) soluble potash. (Official 1951)

K-7. Nitrate of Soda and Potash (sodium and potassium nitrate) is chiefly the sodium and potassium salts of nitric acid. It shall contain not less than fifteen percent (15%) nitrate nitrogen, ten percent (10%) soluble potash and eighteen percent (18% sodium. (Official 1952)

K-8. Sulfate of Potash-Magnesia is a potash salt containing not less than twenty-five percent (25%) soluble potash ($K_2O$) nor less than twenty-five percent (25%) sulfate of magnesia and not more than two and one-half percent (2.5%) chlorine, (Official 1950)

K-9. Double Sulfate of Potash and Magnesia (Langheinite) is a commercial product containing not less than, twenty-one percent (21%) soluble potash ($K_2O$) nor less than fifty-three percent (53%) sulfate of magnesia and not more than two and one-half percent (25%) chlorine. (Official 1950)

K-10. Sulfate of Potash (commercial potassium sulfate) is a potash salt containing not less than forty-eight percent (48%) soluble potash ($K_2O$), chiefly as sulfate, and not more than two and one-half percent (2.5%) chlorine. (Official 1950)

K-11. Kelp—(seaweed) is the dried marine algae of the botanical divisions of Rhodophyta (red algae), Phaeophyia (brown algae), and Chlorophyta (green algae). (Offical 1992)

Micronutrients and secondary nutrients, including, but not limited to:

Compounds containing more than 1% by dry weight of the following micronutrients and secondary nutrients:
Zinc,
Manganese,
Magnesium,
Iron,
Calcium,
Sulfur,
Boron,
Cobalt,
Chlorine,
Copper,
Molybdenum,
Sodium,
Others included which are incorporated by reference in its entirety from the AAPFCO guide, 1998.

The deposition agents of the present invention include, but are not limited to:

Polymeric deposition agents, including but not limited to
polyarcylamides or their copolymers or derivatives, polymers and copolymers of acrylic acid and methacrylic acid or their salts,
polymethacrylamides or their copolymers or derivatives,
polyacrylonitriles, their hydrolysis products, copolymers, or derivatives polyvinyl polymers, copolymers, or derivatives, Natural gums, including but not limited to
Non-derivatized guar gum, cationic guar gum, and non-cationic guar gum, and mixtures, thereof,
Xantham gum,
Gum acacia,
Gum Tragacanth,
Gum Arabic.

The Oil or oil substitutes include but are not limited to:
Alkylated fatty acid esters, include but are not limited to:
Methylated fatty acids, including but not limited to:
Methylated C6–19 fatty acids,
Methylated Tall oil fatty acids,
Methylated Oleic acid, Methylated Linoleic acid,
Methylated Linolenic acid,
Methylated Stearic acid,
Methylated Palmitic acid,
And blends thereof,
Ethylated fatty acids, include but are not limited to:
　Ethylated C6–19 fatty acids,
　Ethylated Tall oil fatty acids,
　Ethylated Oleic acid,
　Ethylated Linoleic acid,
　Ethylated Linolenic acid,
　Ethylated Stearic acid,
　Ethylated Palmitic acid,
　And blends thereof,
Butylated fatty acids, include but are not limited to:
　Butylated C6–19 fatty acids,
　Butylated Tall oil fatty acids,
　Butylated Oleic acid,
　Butylated Linoleic acid
　Butylated Linolenic acid,
　Butylated Stearic acid,
　Butylated Palmitic acid,
　And blends thereof;
Alkylated natural oils, include but are not limited to:
Alkylated soybean oil, including, but limited to:
　Methylated soybean oil,
　Ethylated soybean oil,
　Butylated soybean oil,
　And blends thereof;
Alkylated canola oil, include but are not limited to:
　Methylated canola oil,
　Ethylated canola oil,
　Butylated canola oil,
　And blends thereof;
Alkylated coconut oil, include but are not limited to:
　Methylated coconut oil,
　Ethylated coconut oil,
　Butylated coconut oil,
　And blends thereof,
Alkylated sunflower oil, include but are not limited to:
　Methylated sunflower oil,
　Ethylated sunflower oil,
　Butylated sunflower oil,
　And blend thereof;
Hydrocarbon oils include but are not limited to:
Mineral Oils, including but are not limited to:
　Paraffinic mineral oils,
　Naphthenic mineral oils,
　Aromatic mineral oils,
　And blends thereof;
Vegetable oils, include but are not limited to:
　Soybean oil,
　Canola oil,
　Cottonseed oil,
　And blends thereof;
Fatty acids, include but are not limited to:
　C6–19 fatty acids,
　Tall oil fatty acids,
　Oleic acid,
　Linoleic acid,
　Linolenic acid,
　Stearic acid,
　Palmitic acid,
　And blends thereof;
　Polybutenes
Epoxified seed oils include but are not limited to:
　Epoxified soybean oil and
　Other oils or oil substitutes The oil can contain at least one of the above oils or its equivalent. The oil can also be a blend of at least two oils. When an oil is used, a surfactant or emulsifier must also be used if the composition is intended for aqueous based sprays.

Oil based compositions of this invention may optionally contain thickening agents to improve formulation stability. These thickening agents include but are not limited to:
　Silicon containing thickeners, such as:
　　Precipitated silicas or
　　Precipitated silicates.

Oil based compositions of this invention may contain water, but this is generally not required until the end user adds the concentrate to water for final use. The defoamers of the present invention include, but are not limited to:
　Silicone based defoamers which are described in U.S. Pat. No. 5,964,917, which is incorporated by reference in its entirety herein for all useful purposes. This invention can be practiced with or without the use of silicone defoamers.

The present invention allows for a wide range of compositions under the following limitations:
The composition contains
　1–99% by weight of at least one water soluble or water insoluble fertilizer.
　　preferably less than 87.5% of a nitrogenous fertilizer or 10–99% of a non-nitrogenous fertilizer
　　　more preferably 15–85% of a nitrogenous fertilizer or 15–95% of a non-nitrogenous fertilizer
　　　　most preferably 35–75% of a nitrogenous fertilizer or 25–95% of a non-nitrogenous fertilizer.
　0.5–99% by weight of a deposition agent
　　preferably 0.5–50% of a deposition agent
　　　most preferably 12.5–40% of a deposition.
　where said deposition agent is preferably non-derivatized guar gum, cationic guar gum, or non-cationic guar gum, or mixtures, thereof, or polyacrylamide or polyvinyl polymers. If the fertilizer contains nitrogenous fertilizer, non-derivatized guar gum, cationic guar gum, and non-cationic guar gum, and mixtures, thereof, gum, and a silicone defoamer, the amount of nitrogenous fertilizer must be less than 87.5% of the total product weight, preferably less than 85%. The formulation can be liquid or dry, most preferably dry. If dry, the powdered ingredients are either dry-blended or ground to a fine powder that will pass through a 30 mesh screen. (This corresponds to a particle that is less than 0.59 millimeters in diameter).

The homogeneous liquid compositions may further have less thin 10% water.

The composition optionally contains one or several of the following
　Additional agricultural adjuvants,
　Defoaming agents,
　Pesticides,
　Buffering agents,
　Surfactants and
　Sequestrants.

If a defoaming agent is used, it is preferably a silicone defoamer used at greater than 12.50%. Most preferably, this silicone defoamer would be used at 12.5–20.%. If a non-silicone defoamer is used, it is preferably used at 0.1–10.0%. Most preferably, a non-silicone defoamer is used at 1.0–5.0%. It is also possible that mixtures of these defoamers can be used.

The following patents and reference, which include several ingredients that can be used according to this invention, are incorporated by reference in its entirety for all useful purposes:

U.S. Pat. No. 5,741,502 Homogeneous, essentially nonaqueous adjuvant compositions with buffering capability U.S. Pat. No. 5,725,630 Dry granular fertilizer blend and a method of fertilizing plants U.S. Pat. No. 5,580,567 Homogeneous, essentially nonaqueous adjuvant compositions with buffering capability U.S. Pat. No. 5,393,791 Homogeneous, essentially nonaqueous adjuvant compositions with buffering capability U.S. Pat. No. 5,234,919 Water soluble, highly active dimethoate formulations in an alcohol/ester solvent system U.S. Pat. No. 5,178,795 Homogeneous, essentially nonaqueous adjuvant compositions with buffering capability U.S. Pat. No. 5,906,961 Alkanolamide spreader-sticker surfactant combination U.S. Pat. No. 5,877,112 Agricultural formulation AAPFCO guide, 1998, (Association of American Plant Food Control Officials, Official Publication Number 51)

Pesticides can also be used in this invention. Pesticides, include but are not limited to:

Water insoluble pesticides include but are not limited to:

Water insoluble Herbicides,

Water insoluble Insecticides,

Water insoluble Fungicides,

Water insoluble Bactericides and

Water insoluble rodenticides.

Water soluble pesticides, include but are not limited to:

Water soluble Herbicides,

Water soluble Insecticides,

Water soluble Fungicides,

Water soluble Bactericides and

Water soluble rodenticides.

The following examples illustrate dry fontudations, liquid formulations containing water and oil based formulations. Examples 1–3 are dry based formulations. Examples 4–7 are dry formulations put into liquid form. These formulations contain water. Example 8 is an oil based formulation. Some examples of the composition include

EXAMPLE 1

| Ingredients: | % by weight |
| --- | --- |
| Ammonia sulfate | 50.0% |
| Agrho DR-2000 | 37.5% |
| Silicone defoamers | 1.0% |
| Buffering agents | 11.5% |

The composition in example 1 was made by dry blending the materials. No change is anticipated in the utility of this composition based on manufacturing temperature, pressure, or grinding.

The buffering agent in Example 1 is citric acid and the Agrho DR-2000 is a modified guar gum. Agrho DR-2000 functions as a drift control agent and deposition agent. This formulation also contains a silicone based defoamer. This formulation is used in an aqueous based spray at the rate of 0.5–2.0 pounds per 100 gallons of total spray volume.

Because of the lower use rates of this product as compared with formulations produced under U.S. Pat. No. 5,964,917, formulas made like example 1 are easier to use. The time required for dissolution of this new formulation is about ½ of the time required for that of the prior art. The buffering agents also enhance the pesticide activity of many herbicides and insecticides. The pH of the prior art formulations was about neutral, while Example 1 gives a pH of 3.0 at 0.5% in water.

EXAMPLE 2

| Ingredients: | % by weight |
| --- | --- |
| Mono-Potassium phosphate | 93.0% |
| Agrho DR-2000 | 6.0% |
| Silicone defoamer | 1.0% |

In example 2, the ammonia salts have been completely replaced by mono-potassium phosphate (MKP). MKP has shown not only buffering ability, but the ability to tie up metal cations as well or better than ammonia sulfate. This is an important point for many herbicides, such as glyphosate, which can be tied up by cations in spray water. The use rate of Example 2 is 6–20 pounds per 100 gallons of total spray solution and is intended for aqueous based sprays.

EXAMPLE 3

| Ingredients: | % by weight |
| --- | --- |
| Ammonia sulfate | 93.0% |
| Gum acacia | 6.0% |
| Silicone defoamer | 1.0% |

In example 3, the guar gum used in prior art formulations has been replaced by gum acacia. This alternate gum is often less expensive than guar gum and yet behaves in essentially the same way. Here is no buffering agent added or any real buffering ability afforded by the use of ammonia sulfate. The use rate of Example 3 is 6–20 pounds per 100 gallons of total spray solution and is intended for aqueous based sprays.

EXAMPLE 4

| Ingredients: | % by weight |
| --- | --- |
| Water | 50.0% |
| Ammonia sulfate | 49.0% |
| Agrho DR-2000 | 1.0% |

In example 4, the formulation is put into liquid form. This greatly improves the ease of use of the composition.

EXAMPLE 5

| Ingredients: | % by weight |
| --- | --- |
| Water | 50.0% |
| Mono-potassium phosphate | 48.0% |
| Agrho DR-2000 | 1.0% |
| Silicone defoamer | 1.0% |

In example 5, the components of example 2 are dissolved into water. Again, this greatly improves the ease of use of the formulation.

EXAMPLE 6

| Ingredients: | % by weight |
| --- | --- |
| 2,4-D Amine Tech | 65.0% |
| Polyacrylamide polymers | 2.0% |
| Monopotassium phosphate | 10.0% |
| Water | 23.0% |

EXAMPLE 7

| Ingredients: | % by weight |
| --- | --- |
| Isopropylamine salt of glyphosate | 65.0% |
| Polyacrylamide polymers | 3.0% |
| Monopotassium phosphate | 15.0% |
| Water | 17.0% |

In examples 6 and 7, the polyacrylamide polymers act as a drift reduction agent and deposition agent. 2,4-D amine and glyphosate are water-soluble herbicides.

EXAMPLE 8

| Ingredients | % by weight |
| --- | --- |
| Mineral oil | 86.0% |
| Agrho DR-2000 | 5.0% |
| Emulsifier | 5.0% |
| Aerosil R-972 | 4.0% |

In example 8, the formulation is also in liquid form. In this case, oil has replaced the fertilizers in prior formulations. Oil based products are well known to enhance the effectiveness of many pesticides. Aerosil R-972 is a silicon-based thickening agent specifically designed for use in hydrophobic formulations. The emulsifier is a surfactant and helps the formulation readily disperse in aqueous based spray solutions. The use rate of Example 8 is 0.25–2.0% volume to volume. It is designed to be used in aqueous based sprays.

All the references discussed in this application are incorporated by reference in their entirety for all useful purposes.

While there is shown and described certain specific structures embodying the invention, it will be manifest to those skilled in the art that various modifications and rearrangements of the parts may be made without departing form the spirit and scope of the underlying inventive concept and that the same is not limited to the particular forms herein shown and described.

We claim:

1. An oil based homogenous liquid concentrate agricultural composition comprising
   (a) at least one oil, and
   (b) a natural gum
   with the proviso that there is no added water present and less than 10% by weight water in the composition and said oil is present in the composition in an amount greater than said water and said composition is combined with a pesticide.

2. The composition as claimed in claim 1, wherein said natural gum is a non-derivatized guar gum, cationic guar gum, non-cationic guar gum or mixtures thereof.

3. The composition as claimed in claim 2, wherein said oil is mineral oil or paraffinic petroleum.

4. The composition as claimed in claim 3, which further comprises an oil thickener which is silicon based.

5. The composition as claimed in claim 1, wherein said pesticide is a herbicide, an insecticide, a fungicide, a bactericide or a rodenticide.

6. A method of delivery the benefits of natural gum in liquid oil based compositions which comprises spraying a plant with the composition as claimed in claim 1.

7. A homogenous liquid composition comprising
   a) at least one oil and
   b) a natural gum is a non-derivatized guar gum, cationic guar gum, non-cationic guar gum or mixtures thereof and
   with the proviso that there is less than 10% by weight water present in the composition and the liquid composition is combined with a pesticide.

8. The composition as claimed in claim 7, wherein said oil is mineral oil or paraffinic petroleum.

9. The composition as claimed in claim 7, which further comprises an oil thickener which is silicon based.

10. The composition as claimed in claim 7, wherein said pesticide is a herbicide, an insecticide, a fungicide, a bactericide or a rodenticide.

11. A homogenous liquid agricultural composition comprising
    a) at least one oil, and
    b) a natural gum
    with the proviso that there is less than 10% by weight water present in the composition and said oil is an alkylated fatty acid ester, hydrocarbon oil, alkylated natural oil, fatty acid, polybutene or epoxified seed oil, and said composition is combined with a pesticide.

12. The composition as claimed in claim 11, wherein said oil is methylated C6–19 fatty acids, methylated tall oil fatty acids, methylated oleic acid, methylated linoleic acid, methylated linolenic acid, methylated stearic acid, methylated palmitic acid, blends of the methylated acids, ethylated C6–19 fatty acids, ethylated tall oil fatty acids, ethylated oleic acid, ethylated linoleic acid, ethylated linolenic acid, ethylated stearic acid, ethylated palmitic acid, blends of the ethylated acid, butylated C6–19 fatty acids, butylated tall oil fatty acids, butylated oleic acid, butylated linoleic acid, butylated linolenic acid, butylated stearic acid, butylated palmitic acid, blends of the butylated acids, fatty acid, polybutene or hydrocarbon oil.

13. The composition as claimed in claim 12, wherein said natural gum is a non-derivatized guar gum, cationic guar gum, non-cationic guar gum or mixtures thereof.

14. The composition as claimed in claim 12, wherein said oil is mineral oil or paraffinic petroleum.

15. The composition as claimed in claim 12, which further comprises an oil thickener which is silicon based.

16. The composition as claimed in claim 11, wherein said pesticide is a herbicide, an insecticide, a fungicide, a bactericide or a rodenticide.

* * * * *